Figure 1:
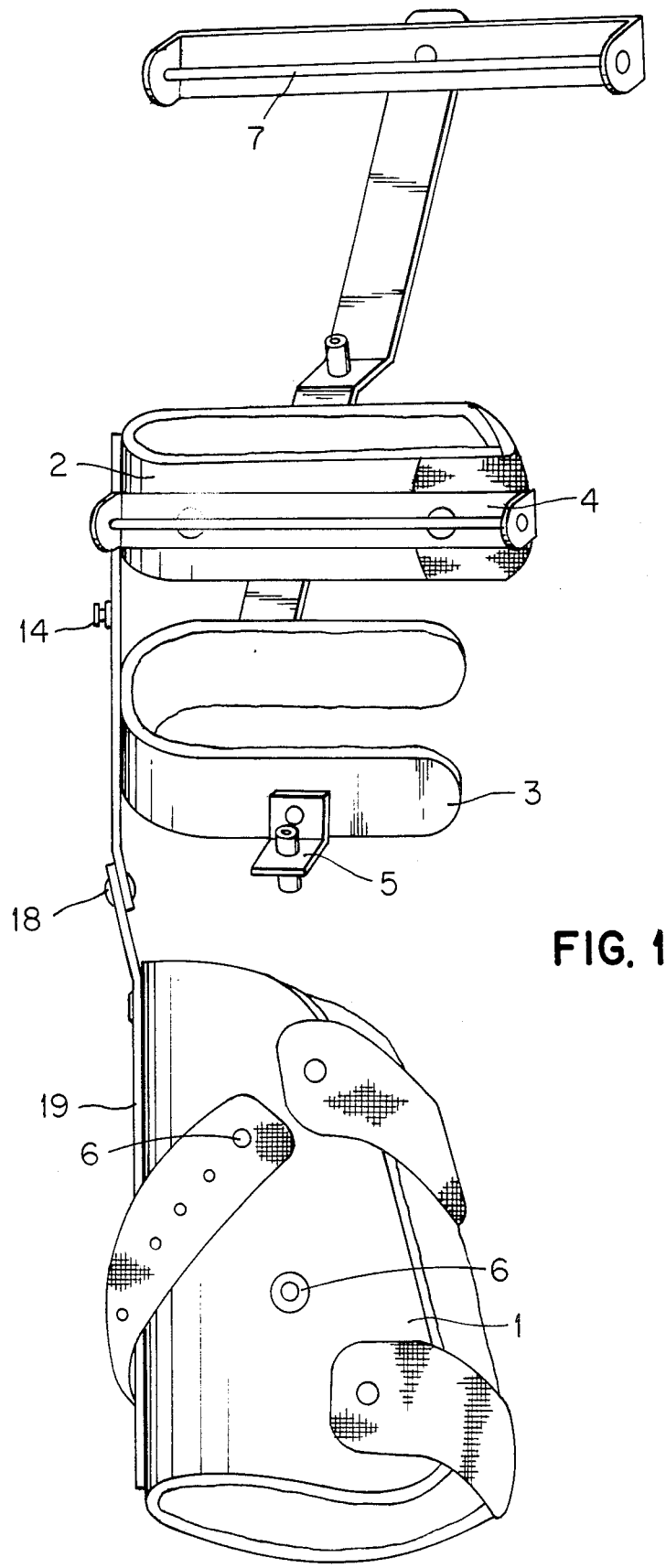

United States Patent [19]

Aymerica del Valle et al.

[11] Patent Number: 4,809,688
[45] Date of Patent: Mar. 7, 1989

[54] SINERGIC SPLINT FOR EARLY MOBILIZATION OF THE FLEXOR TENDONS OF THE HAND

[75] Inventors: Alejandro A. Aymerica del Valle, Vedado; Pablo A. P. Capdet, Marianao; Francisco A. F. Suarez, Marianao; Efrain G. Aguado, Marianao, all of Cuba

[73] Assignee: Empresa Cubana Importadora Y. Exportadora of Products Medicos, T/A Medicuba, Havana City, Cuba

[21] Appl. No.: 38,850

[22] Filed: Apr. 15, 1987

[30] Foreign Application Priority Data

Apr. 22, 1986 [CU] Cuba .......................... 74/86

[51] Int. Cl.$^4$ .................................. A61F 5/04
[52] U.S. Cl. ........................ 128/88; 128/77; 128/84 C
[58] Field of Search ............... 128/87 R, 87 A, 88, 128/89 R, 77, 84 R, 84 C, 85

[56] References Cited

U.S. PATENT DOCUMENTS

| 2,767,708 | 10/1956 | Keropian | 128/77 |
| 2,832,334 | 4/1958 | Whitelaw | 128/77 X |
| 4,602,620 | 7/1986 | Marx | 128/77 |
| 4,644,938 | 2/1987 | Yates et al. | 128/77 X |

FOREIGN PATENT DOCUMENTS 2576512 8/1986 France ................... 128/77

OTHER PUBLICATIONS

Swanson Post-Operative Hand Splint, The Pope Brace Company, 7/1972.

*Primary Examiner*—Robert A. Hafer
*Assistant Examiner*—Kevin G. Rooney
*Attorney, Agent, or Firm*—Lackenbach Siegel Marzullo & Aronson

[57] ABSTRACT

This invention relates to the field of health and in particular to the specialties of hand surgery, orthopaedics and traumatology, and is directed to a sinergic split for early mobilization of the flexor tendons of the hand.

3 Claims, 3 Drawing Sheets

SINERGIC SPLINT FOR EARLY MOBILIZATION OF THE FLEXOR TENDONS OF THE HAND

This invention relates to the field of health and in particular to the specialties of hand surgery, orthopedic surgery and traumatology. Generally, the secondary repair surgery of the hand's flexor tendons is very uniform and whenever possible, the majority of the surgeons prefer the free tendinous graft. Surgery is followed by a period of immobilization of 2-3 weeks, usually with a plaster splint or rigid metallic or plastic splints, used with the intention of preventing tearing or ruptures of the tendon's suture, and a possible appearance of a sympathetic distrophy during the immediate post operatory period after which the rehabilitation program is begun.

The deficiencies of this type of surgery rest upon the fact that the expected results are not always obtained because of the formation of tendinous adherences and articulation rigidities caused by the period of immobilization of the patient's hand; the rehabilitating assistance is prolonged for a period of 4-6 months; the period of labor incapability is prolonged and a high percentage of successive interventions to improve results are required.

Bibliography: MILFORD, LEE. MD. "Campbell's Orthopedic Surgery" Vol. I Chapter 4, page 265; Editorial Intermédica; Buenos Aires, Argentina 1975 5th Edition. LANGE, MAX. MD. "Orthopedic Surgery" Superior Extremity, Chapter 5 page 432, 1st Edition, Editorial Labor S. A. Barcelona, Spain 1968. MICHON, J. VILAIN, R. "Tendinous Injuries in Hand Traumatisms" Chapter 3 page 22, Toray-Masson Editorial, Barcelona, Spain, 1976. PULVERTAFT, R. GUY, "Tendon Grafting for the Isolated Injury of flexor Digitorum Profundus". Bulletin of the Hospital for joint disease Orthopaedic Institute. Vol. 44 #2 page 424-434, 1984.

Other authors use the long tendinous graft, combining it with precocious and passive mobilization of the corresponding finger, maintaining the wrist immobilized for three weeks; with the same deficiencies already expressed. VERDAN, C. "Primary Repair of Flexor Tendons". The Journal of Bone and Joint Surgery. Vol 43-A No. 4 page 647, June 1960. PULVERTAFT, R. G. "Tendon graft for flexor tendon injuries in the fingers and thumb". The Journal of Bone and Joint Surgery. Vol. 38-B page 175-194, 1956. KELI NERT, H. E. "Flexor tendon injuries". The Surgical clinics of North America 61 (2) page 267-286. April 1981.

The objective of this invention is to create a splint that would be placed on the patient 48 hours after the operation and that would guarantee the continuous or intermittent sliding of the graft, in such a way as to permit the rupture of the fibrine bridges inevitable in all healing processes and to stimulate the formation of fibrous tissue rich in elastic elements in order to minimize the development of blocking adherences without risks of rupture of sutures, or tearing of the tendinous graft.

The essence of this invention consists of a splint composed of: carpal support; universal palmar pully; anterior carpal pully; anterior posts of fixation; universal dorsal pulley; arm of the universal dorsal pulley; guide pulley of the arm; dorsal carpal pulley; fixation dispositive of the arm of the motor; platform of support of the motor's body; posterior fixation posts; fixation post of the immobilizing belt; adhesive closing; rubber foam lining; immobilizing belt; joint of the axis of the splint; axis of the splint; inactivation post of the immobilizing belt; traction means of the passive extension dispositive; Kirschner's wire; traction means of the passive flexion dispositive.

REPRESENTATIVE FIGURES

Figure 2:
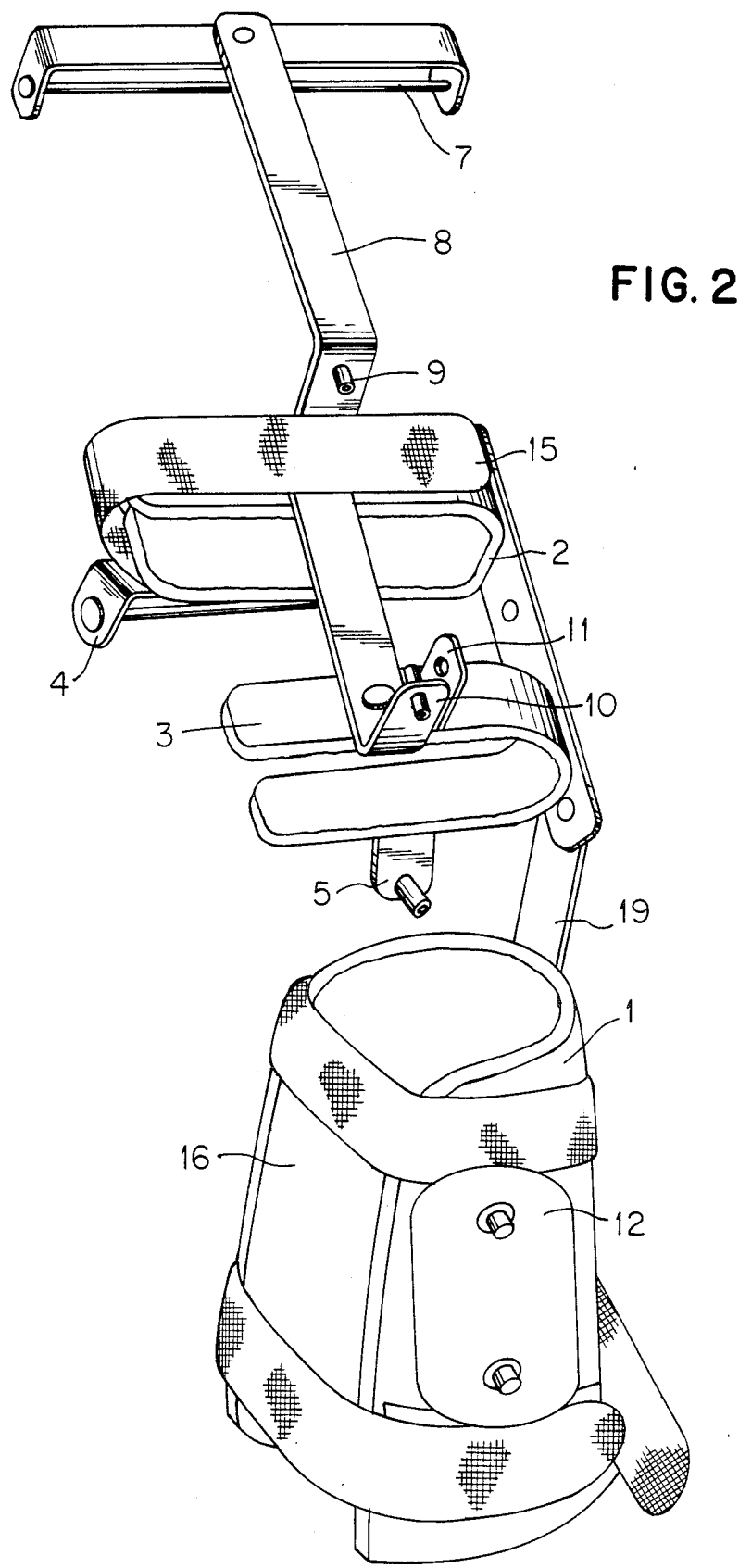
Figure 3:
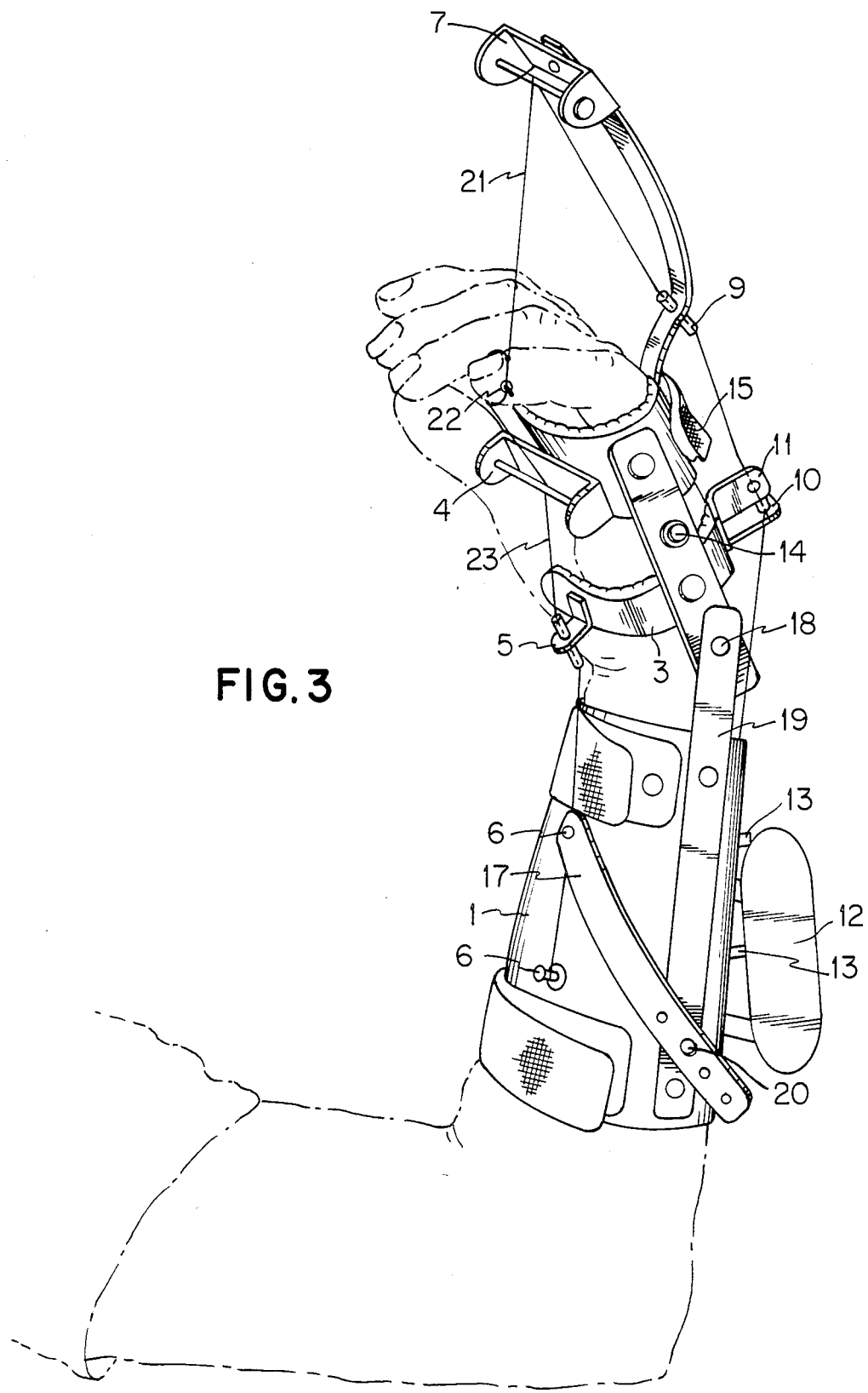

FIG. 1 Isometric palmar view of the splint
FIG. 2 Isometric dorsal view of the splint
FIG. 3 Isometric antero-medial view of the splint The invention comprises a dynamic splint of sinergic movements formed by: antebrachial support (1); palmar support (2); carpal support (3); universal palmar pulley (4); anterior carpal pulley (5); posts of anterior fixation (6); universal dorsal pulley (7); Arm of the universal dorsal pulley (8); arm's guide pulley (9); dorsal carpal pulley (10)-dispositive of fixation of the motor's arm (11); fixation platform of the motor's body (12); posterior fixation posts (13); fixation post of the immobilizing belt (14); adhesive closing (15); rubber foam lining (16); immobilizing belt (17); joint of the splint's axis (18); splint's axis (19); inactivating post of the immobilizing belt (20): traction means of the passive extension dispositive (21); Kirschner's wire (22); traction means of the passive flexion dispositive (23); articulated by the cubital border of the wrist (18 FIG. 1), and two digital traction dispositives added, one palmar (4, 5, 6 FIG. 1) and another dorsal (7, 8, 9, 10, 12, FIG. 2), which by means of the passive or active flexion and extension of the wrist accompliches the sliding of the tendinous graft without tension.

The present invention provides a sinergic splint for early mobilization of the flexor tendons of the hand comprising (1) antebrachial support means at one end of said splint;
(6) anterior fixation post on said antebrachial support means;
(7) universal dorsal pulley attached to the other end of said splint by universal dorsal pulley arm (8);
(5) anterior carpal pulley on said splint located between said anterior fixation post (6) and said universal dorsal pulley (7);
(4) universal palmar pulley on said splint located between said anterior carpal pulley (5) and said universal dorsal pulley
(9) guide pulley on the dorsal pulley arm (8);
(13) posterior fixation post on said splint at the same end as is located said anterior fixation post (6); and
(10) dorsal carpal pulley on said splint and located between said guide pulley (9) and said posterior fixation post (13);

whereby whenever said splint is placed on said hand, a traction means (23) of the passive flexion dispositive can be anchored to a Kirschner's wire (22) attached to a finger of said hand, and then passed through said universal palmar pulley (4) and contacts the anterior carpal pulley (5) and is fastened to the anterior fixation posts (6); and whereby an anchorage to said Kirschner's wire (22) in said finger is realized by means of traction for the extension (21) which is introduced by the universal dorsal pulley (7) which means (21) is passed over arm guide pulley (9), and over dorsal carpal pulley (10) and is then fastened to the posterior fixation posts (13).

This variation implicitly carries the elimination of the plastered bandage or any other permanent immobilization system. The intimate action mechanism of the splint is given by the fact that when the active or passive extension of the wrist joint takes place, we are separating the proximal and distal suture points. As the tendon is not elastic, it is obliged to flex the finger by traction of the distal phalanx provoking the development of the cascade of the corresponding digital flexion. Nevertheless, the tendinous graft is not capable of resisting the imposed tension caused on one hand by the tone of the muscles that participate in the formation of the finger's extensor apparatus and on the other, the increase of the resistance derived from the surgical trauma with its consequent pain and local edema. In such a way, the splint has incorporated the dispositives that guarantee the gradual passive flexion of the finger simultaneously with the extension of the wrist and viceversa. This passive flexion of the finger(s) participating is realized with a certain grade of palmar hipercorrection, that is, the finger is flexed faster than the extension of the wrist with the objective of avoiding additional tension to the graft. The dispositive of digital traction (dorsal and palmar) uses as means of traction any synthetic suture not absorbable which anchors itself to the wire transfixion realized in the distal phalanx.

From the surgical point of view, a long graft free of tendons is performed on these patients using as way of access a zig-zag or the medio lateral way. Before the operation a transfixion of the distal phalanx is accomplished using a Kirschner's wire (22 FIG. 3) to serve as anchorage to the traction means of the digital mobilization dispositives of the splint. The graft is performed according to the same technical norms required for the short graft but in the present invention, it must be longer so as to be sutured proximally in the anterior face of the wrist. The distal suture is conventional. After 48 hours the splint is put in place and the mobilization is begun according to the criteria of the continuous passive movement. It can also be used manually, intermittently with a nocturnal rest in which case the splint must be fixed in flexion position with the immobilizing belt (17), displacing it from its fixture the inactivation post (20 FIG. 3) to the belt fixation post (14) using as pivot the post of the most distal anterior fixation (6 FIG. 3). To place the splint, after having closed the adhesive brooch (15 FIG. 2), the wrist is placed in the maximus passive flexion with the fingers also in the maximus passive extension, then the means of traction is anchored to the Kirschner's wire (22 FIG. 3) and it is passed through the universal palmar pulley (4), by the anterior carpal pulley (5) and in a slight hipercorrection in flexion it is fastened to the anterior fixation posts (6). Afterwards, and always in the same position previously described, the anchorage to the Kirschner's wire in the finger is realized (22) by the means of traction for the extension, it is introduced by the universal dorsal pulley (7), it is passed by the arm's guide (9), and by the carpal dorsal pulley (10). After realizing this operation, it is softly tractioned and tensed and afterwards it is fastened to the posterior fixation posts (13). The splint is maintained for thirty days after which it is retired and the active rehabilitation is begun. The digital traction dispositives function simultaneously and in synergic way with the wrist's flexion and extension movements and are formed by a system of pulleys that once the corresponding means of traction are fixed, then the passive mobilization of the fingers begins automatically with the displacement of the wrist joint, either in an active voluntary way, or if so prefered, in a passive way using a motor which is fixed to the platform (12 FIG. 3) using an adhesive plastic closing, and its axis is fixed in the fixation dispositive of the motor's arm (11 FIG. 3). In this manner the sinergic passive movement of the fingers with the corresponding movements of the wrist can be achieved.

The final result of this precocious mobilization is the improvement of the final active mobilization and the shortening of the convalescence period, and simultaneously there is the shortening of the period of institutional rehabilitation assistance. Also it considerably minimizes the reinterventions fundamentally to the tenolisis.

The results obtained in some patients are described as follows:

Patient No. 1

Section of both flexors of the fourth finger of the left hand, of six month of evolution. A long tendon graft was realized, and anchored to the profound flexor muscle. The splint was retired after 30 days. Total time of active rehabilitation 50 days. Complete recovery 80 days after surgery. Excellent result.

Patient No. 2

Section of both flexors of the fifth finger. A long tendinous graft was realized. Splint retired after 30 days. Total time of active rehabilitation 35 days. Final result, good.

We claim:

1. A sinergic splint for early mobilization of the flexor tendons of the hand comprising
    antebrachial support means at one end of said splint;
    anterior fixation post on said antebrachial support means;
    universal dorsal pulley attached to the other end of said splint by universal dorsal pulley arm;
    anterior carpal pulley on said splint located between said anterior fixation post and said universal dorsal pulley;
    universal palmar pulley on said splint located between said anterior carpal pulley and said universal dorsal pulley;
    guide pulley on the dorsal pulley arm;
    posterior fixation post on said splint at the same end as is located said anterior fixation post; and
    dorsal carpal pulley on said splint and located between said guide pulley and said posterior fixation post;
    whereby whenever said splint is placed on said hand, a traction means of the passive flexion dispositive can be anchored to a Kirschner's wire attached to a finger of said hand, and then passed through said universal palmar pulley and contacts the anterior carpal pulley and is fastened to the anterior fixation posts; and whereby an anchorage to said Kirschner's wire in said finger is realized by means of traction for the finger extension which is introduced by the universal dorsal pulley which means is passed over arm guide pulley, and over dorsal carpal pulley and is then fastened to the posterior fixation posts.

2. The splint of claim 1, further comprising a palmar support adjacent to universal palmar pulley.

3. The splint of claim 1, further comprising a carpal support adjacent to said anterior carpal pulley.

* * * * *